United States Patent [19]

Thies et al.

[11] 4,256,642

[45] Mar. 17, 1981

[54] PHARMACEUTICALLY ACTIVE 2,9-DIOXATRICYCLO[4,3,1,0$^{3,7}$] DECANES

[75] Inventors: Peter Willibrord Thies, Hanover; Akiji Asai, Wennigsen, both of Fed. Rep. of Germany

[73] Assignee: Kali-Chemie Pharma GmbH, Hanover, Fed. Rep. of Germany

[21] Appl. No.: 51,499

[22] Filed: Jun. 25, 1979

Related U.S. Application Data

[62] Division of Ser. No. 884,854, Mar. 9, 1978, Pat. No. 4,189,437, which is a division of Ser. No. 732,791, Oct. 15, 1976, Pat. No. 4,089,971.

[30] Foreign Application Priority Data

Oct. 22, 1975 [DE] Fed. Rep. of Germany ....... 2547205

[51] Int. Cl.$^3$ ............................................ C07D 319/14
[52] U.S. Cl. ..................... 260/340.3; 424/278
[58] Field of Search ...................................... 260/340.3

[56] References Cited

U.S. PATENT DOCUMENTS

| | | | |
|---|---|---|---|
| 3,812,154 | 5/1974 | Thies | 260/340.3 |
| 3,917,651 | 11/1975 | Thies | 260/340.3 |
| 4,016,176 | 4/1977 | Thies | 260/340.3 |
| 4,089,971 | 5/1978 | Thies | 424/278 X |
| 4,117,148 | 9/1978 | Thies et al. | 260/340.3 X |
| 4,141,988 | 2/1979 | Thies et al. | 260/340.3 X |
| 4,158,061 | 6/1979 | Thies et al. | 260/340.3 X |
| 4,182,889 | 1/1980 | Asai et al. | 260/340.3 X |
| 4,189,437 | 2/1980 | Thies et al. | 260/340.3 |

FOREIGN PATENT DOCUMENTS

759840 5/1971 Belgium.

*Primary Examiner*—Ethel G. Love
*Attorney, Agent, or Firm*—Schwartz, Jeffery, Schwaab, Mack, Blumenthal & Koch

[57] ABSTRACT

Pharmaceutically active 2,9-dioxatricyclo[4,3,1,0$^{3,7}$] decanes and the process for their production and the production of various intermediates are disclosed. Pharmaceutical compositions containing an effective amount of the novel compounds and a pharmaceutically acceptable carrier are also disclosed.

11 Claims, No Drawings

PHARMACEUTICALLY ACTIVE 2,9-DIOXATRICYCLO[4,3,1,0³,⁷] DECANES

This application is a division of application of Ser. No. 884,854, filed Mar. 9, 1978, now U.S. Pat. No. 4,189,437, which is a division of Ser. No. 732,791, filed Oct. 15, 1976, now U.S. Pat. No. 4,089,971.

BACKGROUND OF THE INVENTION

1. Field of the Invention

This invention relates to certain novel 2,9-dioxatricyclo[4,3,1,0³,⁷]decanes exhibiting pharmaceutical activity, to intermediates useful in the preparation thereof, to processes for preparing the novel compounds, and to pharmaceutical compositions containing the active compounds.

2. Description of the Prior Art

In German Offenlegungsschrifts Nos. (Published Specifications) 19 61 433, 20 27 890, 21 29 507 and 23 06 118 and the corresponding U.S. Pat. Nos. 3,812,154 and 3,917,651, are described 2,9-dioxatricyclo[4,3,1,0³,⁷]decanes which bear in the 8-position an alkoxy or aralkoxy group. These compounds have sedative effects on the central nervous system, as well as hypnotic, narcotic and vasodilating effects.

Compounds such as morphine and morphine-like structures, as well as conventional analgesics, such as methadone, are known to have a strong analgesic effect when administered in adequate doses. The activity of the analgesic is reflected in the relative dosage of the various analgesic compounds and, it is correspondingly often advantageous to administer compounds of increased activity in smaller dosage quantity.

Moreover, compounds having an anorectic effect are widely known such as phenmetrazine, also known by the trademark PRELUDIN. Along with the anorectic effect, compounds of the phenylalkylamine-type possess additional characteristic pharmacological parameters such as toxicity and motor-stimulating effectiveness which, under certain conditions, may interfere with the administration of effective doses.

Many of these known compounds may possess more than one of the above described characteristics and it is, of course, highly advantageous to administer such compounds that produce the most desirable pharmacological effects with the least adverse effects.

SUMMARY OF THE INVENTION

Accordingly, the present invention has as one of its objects, the achievement of a compound exhibiting highly desirable pharmaceutical activity.

It is also an object of the present invention to provide a compound having a stimulating action and an analgesic effect when administered in conventional dosage amounts.

Surprisingly, it has now been found that in accordance with the present invention that certain 8-desalkoxy and 8-desaralkoxy 2,9-dioxatricyclo[4,3,1,0³,⁷]decanes act in general much more strongly on the central nervous system than the corresponding alkoxy and aralkoxy derivatives known in the prior art. This greater activity manifests itself not only in the doses to be administered but also in a strong analgesic effect which substantially equals that of morphine, although the 2,9-dioxatricyclo[4,3,1,0³,⁷]decanes have no structural features of morphine or other conventional analgesics, as for example, the methadone group, to which also the reference substance propoxyphene belongs.

Moreover, the compounds according to the invention have an anorectic effect which is generally superior to that of conventional phenmetrazine without being in any way related to the phenylalkylamines either chemically or in other pharmacological parameters, for example toxicity and motor-stimulating effectiveness.

The pharmaceutically active 2,9-dioxatricyclo[4,3,1,0³,⁷]decanes according to the present invention are represented by the general formula I:

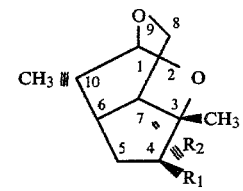

wherein one of $R_1$ and $R_2$ is hydrogen and the other is a hydroxy, acyloxy or carbamyloxy group, or $R_1$ and $R_2$ taken together denote oxygen.

The several compounds according to the present invention which are formed as intermediates in the process for preparing the pharmaceutically active 2,9-dioxatricyclo[4,3,1,0³,⁷]decanes of formula I include the following identifiable compounds which may be isolated and which possess important physiological characteristics:

4-Acetoxy-8-hydroxy-3-halomethyl-10-methylene-2-9-dioxatricyclo[4,3,1,0³,⁷]decane of formula II:

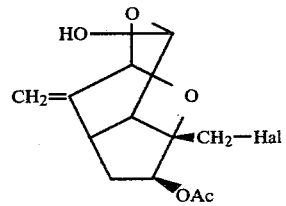

4-Acetoxy-3-halomethyl-10-methylene-8-oxo-2-9-dioxatricyclo[4,3,1,0³,⁷]decane of formula III:

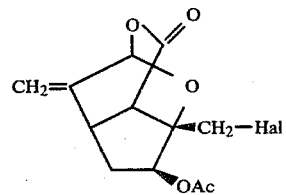

1-Halomethyl-4-methyl-7-acetoxy-2-oxa-bicyclo[3,2,1]-oct-3-en-8-carboxylic acid of formula IV:

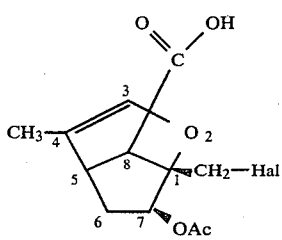

1-Halomethyl-4-methyl-7-acetoxy-8-hydroxymethyl-2-oxabicyclo[3,2,1]oct-3-ene of formula V:

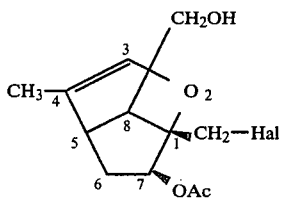

A 4-acetoxy-3-halomethyl-10-methyl-2,9-dioxatricyclo[4,3,1,0$^{3,7}$]decane of the general formula VI:

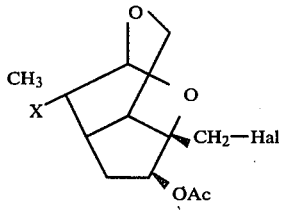

wherein X is iodine or bromine.

4-hydroxy-3,10-dimethyl-2,9-dioxatricyclo[4,3,1,0$^{3,7}$]decane of the general formula VII:

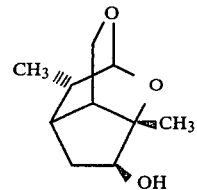

3,10-dimethyl-2,9-dioxatricyclo[4,3,1,0$^{3,7}$]decane-4-one of formula VIII:

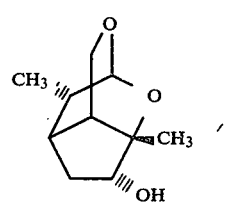

4-α-hydroxy-3,10-dimethyl-2,9-dioxatricyclo[4,3,1,0$^{3,7}$]decane of formula IX:

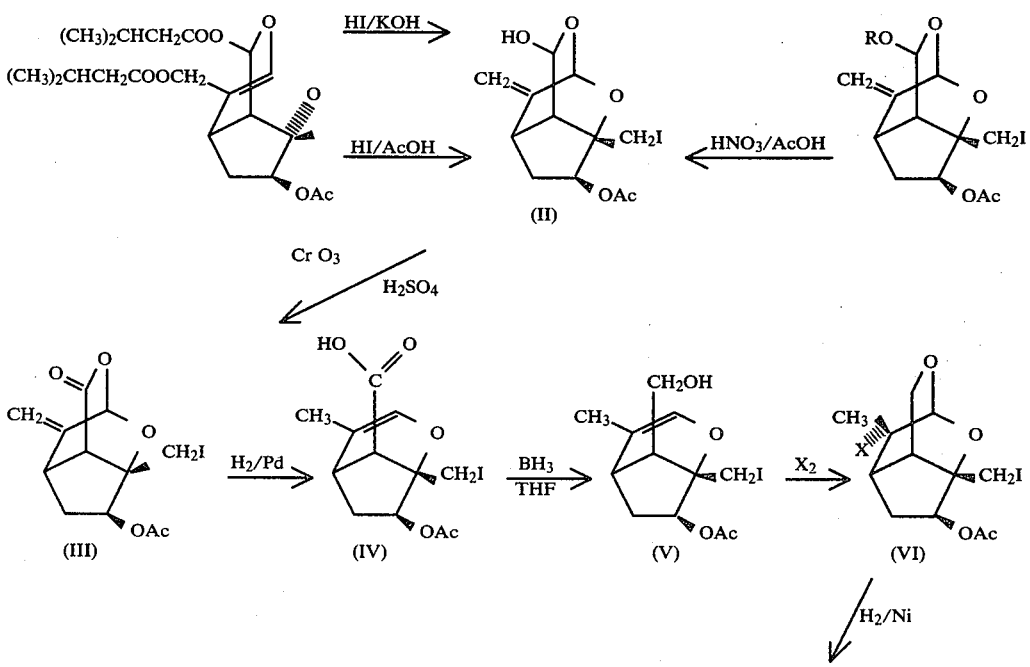

The compounds of the present invention may be prepared according to the general reaction sequence of a preferred embodiment illustrated as follows:

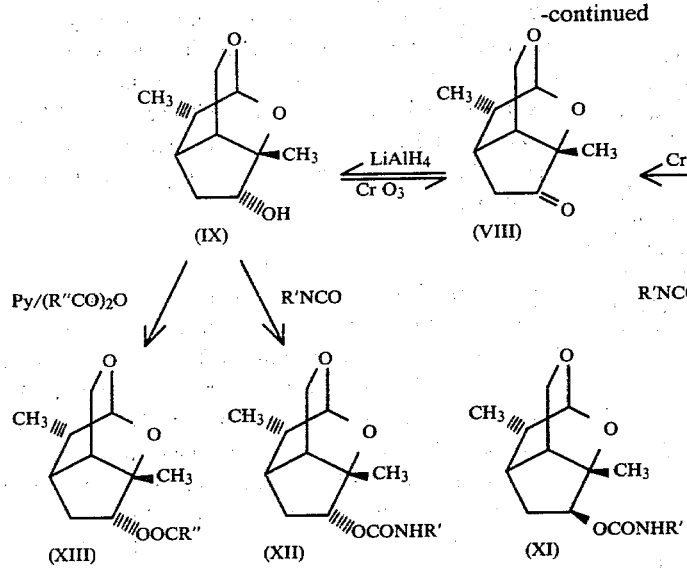
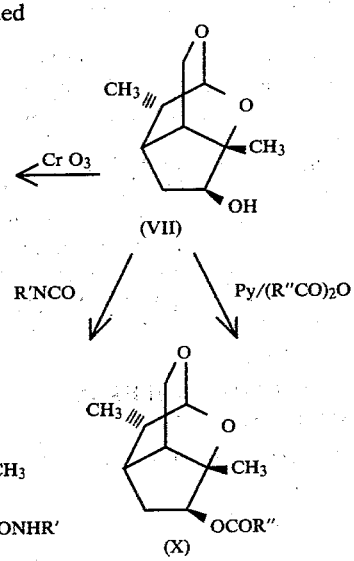

R=alkyl with 1-6 C-atoms or benzyl
R'=alkyl with 1-4 C-atoms or phenyl
R"=alkyl with 1-5 C-atoms As demonstrated in the above reaction sequence, in the first step didrovaltratum or an extract containing didrovaltratum, is reacted with a hydrogen halide, e.g. HI in acetic acid or in alcohol. In the case of reaction in an alcohol the resulting 8-alkoxy- or 8-aralkoxy compound is converted into the corresponding 8-hydroxy compound through splitting of the ether bond by means of nitric acid in acetic acid. In both cases, the resulting 8-hydroxy-3-halomethyl-4-acetoxy-10-methylene-2,9-dioxatricyclo[4,3,1,0$^{3,7}$]decane of formual II is oxidized to give the lactone of formula III. The lactone is converted hydrogenolytically with hydrogen on palladium/charcoal to give 1-halomethyl-4-methyl-7-acetoxy-2-oxa-bicyclo[3,2,1]oct-3-en-8-carboxylic acid of formula IV. The acid of formual IV is reduced with a metal hydride e.g. BH$_3$ to give the primary alcohol of formula V. The alcohol of formula V is converted into 10-halo-10-methyl-3-halomethyl-4-acetoxy-2,9-dioxatricyclo[4,3,1,0$^{3,7}$]decane of formula VI through oxidative cyclisation by means of halogen in a halogenated hydrocarbon. The halogens are split off the product of formula VI with hydrogen on Raney nickel in the presence of a strong base, the ester being hydrolyzed simultaneously, so that 3,10-dimethyl-4-β-hydroxy-2,9-dioxatricyclo[4,3,1,0$^{3,7}$]decane of the formual VII is obtained. The compound of formula VII (if appropriate) is converted with carboxylic anhydride or carboxylic acid chloride or with alkyl isocyanates or carbamic acid esters into the acyloxy or carbamyloxy compound, or (if appropriate) converted through oxidation of the 4-hydroxy group into the decanone of the formula VIII. This latter product (if appropriate) is reduced with a metal hydride e.g. LiAlH$_4$ to give 4-α-hydroxy-decane of the formula IX which (if appropriate) is converted into the acyloxy or carbamyloxy compound with carboxylic anhydride or carboxylic acid chloride or with alkyl isocyanates or carbamic acid esters.

Other reactants may be used in place of those shown in the above reaction sequence. Thus in an alternate embodiment, when preparing II from didrovaltratum (or an extract containing didrovaltratum), instead of hydriodic acid, hydrochloric or hydrobromic acid may also be used. Again, instead of the metal hydrides shown in the reaction sequence in the reduction of the acid IV to the alcohol V or of the decanone VIII to the hydroxy compound IX, other metal hydrides may be used, provided that they leave intact the other functional groups of the molecule and also react sterically in the manner stated. Further, the acid radicals in the esters X and XIII may also originate from saturated or unsaturated carboxylic acids (preferably from those with 1 to 7 C atoms) other than the acetic acid shown; also, the nitrogen in the carbamic esters XI and XII may be substituted not with methyl but with other alkyl groups or with alkylene or aralkyl radicals. The N atom may also be part of a ring system.

The compounds of the present invention may be formulated together with conventional pharmaceutically acceptable carriers or diluents for therapeutic administration.

A significant aspect of the instant invention resides in the discovery that certain 8-desalkoxy 8-desarylalkoxy 2,9-dioxatricyclo[4,3,1,0$^{3,7}$]decanes exhibit enhanced activity as opposed to corresponding analogous compounds of the 8-alkoxy and arylalkoxy derivatives known in the prior art. Accordingly, the pharmaceutically active compounds of the instant invention are employed in pharmaceutical compositions giving analgesic and anorectic results when they are employed alone, or in combination with the usual pharmaceutically acceptable carrier such as those discussed in the aforementioned German Published Specifications and corresponding U.S. patents. The carrier materials may, for instance, be water, a pharmaceutically acceptable vegetable oil, gelatin, lactose, a polyethyleneglycol, starch, magnesium stearate, talcum, etc. The proportions of carrier and active pharmaceutical agents is of course determined by conventional solubility considerations and the chosen route of administration.

Pharmaceutical compounds of this invention can be administered according to this invention by any means as is conventional for analgesic and anorectic compositions. One highly advantageous result of the instant discovery is that, because of the increased activity of the pharmaceutically active compounds of the instant invention, smaller dosage quantities of the active compound may be administered to achieve desirable analgesic results.

For the parenteral application solutions, preferably oily or aqueous solutions may best be used as carriers. However, the compounds can also be applied in suspension or emulsions.

For the enteral application, tablets, capsules or lozenges may be used which may contain the usual additives, for instance preservatives, stabilizers or wetting agents. The compounds may be applied by mouth or by subcutaneous or intravenous injection. For human patients, the preferred single dose for application per os is between 10 and 100 mg. In the case of animals, the dose may be higher.

DESCRIPTION OF THE PREFERRED EMBODIMENTS

The invention is illustrated by the examples which follow:

EXAMPLE 1

Preparation of 4-acetoxy-8-hydroxy-3-iodomethyl-10-methylene-2,9-dioxatricyclo[4,3,1,0$^{3,7}$]decane (II) from a 66% strength didrovaltrate extract.

425 g of extract were dissolved in one liter of acetic acid at 60° C., then a mixture of 130 ml of hydriodic acid (57% strength) and 1 liter of water was added to the solution, and the mixture was left to stand for 2 hours at 60° C., with occasional stirring.

Working up

After addition of 100 g of activated charcoal, suction filtration over Theorit was effected, followed by thorough washing with 4 liters of ether. 3-liters of water were added to the filtrate, thorough shaking was effected, and the ether phase was separated off. This was then washed with alkaline, once with 2 liters of water and once with soda solution (1.5 kg of sodium carbonate in 8 liters of water). The three water phases were then extracted individually 3 times with, in each case, 2 liters of ether. The combined ether phases were dried over 1 kg of sodium sulphate, treated with 100 g of activated charcoal, suction filtered over Theorit and then concentrated in a vacuum at 30°–40° C. in a round flask, with addition of 18 ml of water; II crystallised. After rubbing with ether and filtration over a suction filter, 170 g of crude crystalline product was obtained representing 70% of theoretical yield.

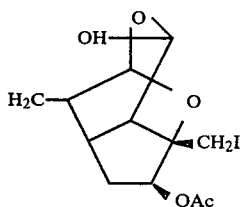
(II)

Empirical Formula: $C_{12}H_{15}O_5I$
Molecular Weight: 366.14
m.p.: 152°–156° C. (Kofler, uncorrected)
$[\alpha]_D^{+22° C.}$: +142° (Methanol)

EXAMPLE 2

Preparation of (II) from 4-acetoxy-3-iodomethyl-10-methylene-8-methoxy-2,9-dioxatricyclo[4,3,1,0$^{3,7}$]decane.

760 g of 4-acetoxy-3-iodomethyl-10-methylene-8-methoxy-2,9-dioxatricyclo[4,3,1,0$^{3,7}$]decane were dissolved at 60° C. in 2 liters of glacial acetic acid, and a mixture of 180 ml of 64% strength nitric acid and 2 liters of water was then added to the solution at room temperature. The mixture remained standing for 2 hours at room temperature, with stirring.

Working up 8 liters of ether and 6 liters of water were added to the reaction mixture and thorough shaking was effected. The ether phase was separated off and washed once with 4 liters of water and then with soda solution (2 kg of sodium carbonate in 6 liters of water). The two water phases and the soda solution were then extracted individually 3 times with, in each case, 4 liters of ether. The combined ether phases were dried over 2 kg of sodium sulphate and treated with 200 g of activated charcoal. Subsequently, suction filtration over Theorit was effected, followed by thorough washing with ether. The filtrate was concentrated in a vacuum at 30°–40° C. in a flask, with addition of 36 ml of water. The residue crystallising was taken up in ether, suction filtered over a frit and thoroughly washed once with ether.

Yield: 660 g (II), that is, 90.2% of the theoretical yield.

EXAMPLE 3

Preparation of 4-acetoxy-3-iodomethyl-10-methylene-8-oxo-2,9-dioxatricyclo[4,3,1,0$^{3,7}$]decane (III) from (II).

366 g of (II) were taken up in 20 liters of ether at room temperature, 1250 ml of oxidation reagent were added dropwise with vigorous stirring, and stirring was then continued for a further 30 minutes.

Preparation of the oxidation reagent 500 g of $Na_2Cr_2O_7.2H_2O$ were taken up in 375.2 ml of 97% strength $H_2SO_4$ at 0° C. and the volume was, with stirring, first made up to about 2400 ml with cold water and then, at room temperature, made up to exactly 2500 ml.

Working up of the oxidation mixture 5 liters of $H_2O$ were added to the reaction mixture and shaking was effected. The ether phase was separated off and washed once with 1 kg of sodium carbonate in 5 liters of water. The water phase and the soda solution were then extracted individually three times, with in each case 3 liters of chloroform. The ether and chloroform phases were dried over sodium sulphate, treated with activated charcoal and then suction filtered over Theorit, washed with chloroform and evaporated in a vacuum. The evaporation residue was taken up with ether; (III) crystallised. It was suction filtered and washed once with ether.

Yield: 310 g (III), that is, 86% of the theoretical yield.

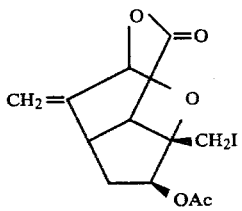

(III)

Empirical formula: C$_{12}$H$_{14}$O$_5$I
Molecular weight: 365.139
m.p.: 163°–168° C. (Kofler, uncorrected)
[α]$_D$$^{+20°}$: +114° (Methanol)

EXAMPLE 4

Preparation of 1-iodomethyl-4-methyl-7-acetoxy-2-oxabicyclo[3,2,1]oct-3-en-8-carboxylic acid (IV) from (III).

100 g of palladium-charcoal (5% strength) were placed in a 2-liter conical flask then suspended with 1 liter of ethanol (absolute) under nitrogen and immediately prehydrogenated for 5 minutes (with stirring) at room temperature and normal pressure. (About 1300 ml of hydrogen were taken up.) Then 182.5 g of (III) dissolved in 1.5 liters of absolute ethanol were added and the mixture was hydrogenated for about 2 hours until the standstill of the hydrogen uptake. Hydrogen consumption: 11200 ml.

Working up

The catalyst was suction filtered over Theorit, washed with absolute ethanol and the filtrate was evaporated at about 30° C. in a vacuum. The residue crystallised immediately; it was triturated with ether, suction filtered, washed with ether and dried.

Yield: 180 g of (IV), that is, 98.2% of the theoretical yield.

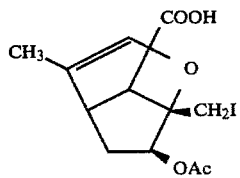

(IV)

Empirical formula: C$_{12}$H$_{15}$O$_5$I
Molecular weight: 366.15
m.p.: 150°–155° C. (Kofler, uncorrected)
[α]$_D$$^{+20}$: +110° (Methanol)

EXAMPLE 5

Preparation of 1-iodomethyl-4-methyl-7-acetoxy-8-hydroxy-methyl-2-oxa-bicyclo[3,2,1]oct-3-en (V) from (IV).

73.2 g of (IV) were dissolved in 200 ml of tetrahydrofuran, and 1 liter of boron hydride in tetrahydrofuran (1% strength) was added slowly to the solution at −25° C., with stirring and nitrogen. The mixture was then left to stand for 2 hours at +10° C.

Working up

With stirring and nitrogen, first 30 ml of triethylamine were added slowly at −25° C., and then 80 ml of water were very slowly added dropwise to the mixture, which was evaporated at 30°–40° C. The residue was taken up in ether, washed twice with 700 ml of water and once with (90% saturated) soda solution. The 3 aqueous phases were individually extracted 3 times with ether. The combined ether phases were treated with sodium sulphate and activated charcoal, suction filtered over Theorit and then evaporated at 30°–40° C.

Yield: 153 g of oily crude product (V). This was used without further purification for the preparation of (VI).

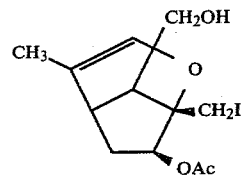

(V)

Empirical formula: C$_{12}$H$_{17}$IO$_4$
Molecular weight: 352.17

EXAMPLE 6

Preparation of 4-acetoxy-10-bromo-3-iodomethyl-10-methyl-2,9-dioxatricyclo[4,3,1,0$^{3,7}$]decane (VI) from (V).

153 g of (V) (crude product) were dissolved in 1100 ml of methylene chloride in a brown round flask and a mixture (which beforehand was cooled to −75° C.) of 53 ml of bromine and 110 ml of methylene chloride was added slowly, with vigorous stirring.

Working up

After completion of addition of bromine, neutralization was immediately effected slowly with a mixture of 168 ml of triethylamine and 110 ml of methylene chloride; washing was effected once in each case with water, with saturated Na$_2$S$_2$O$_5$ solution and potassium carbonate solution. The three aqueous phases were individually extracted three times with methylene chloride. The combined methylene chloride phases were treated with sodium sulphate and activated charcoal, suction filtered over Theorit and evaporated at 30° C. in a brown round flask.

Yield: 186 g of oily crude product.

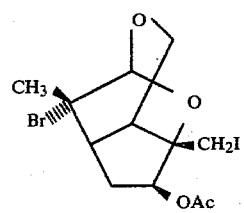

(VI)

Empirical formula: C$_{12}$H$_{16}$BrIO$_4$
Molecular weight: 431.07

EXAMPLE 7

Preparation of 4-β-hydroxy-3,10-dimethyl-2,9-dioxatricyclo[4,3,1,0$^{3,7}$]decane (VII) from (VI).

86 g of water-moist Raney nickel were prehydrogenated in methanol for 1 minute at −25° C., 51.5 g of sodium hydroxide were dissolved in a little water (200 ml) and diluted at 0° C. with 200 ml of methanol. This sodium hydroxide solution was added to the Raney nickel suspension then further stirred for about 2 minutes at −25° C. under hydrogen. 186 g of crude product of (VI) were then dissolved in 200 ml of methanol and added to the Raney nickel suspension at 0° C. Subsequently, hydrogenation was effected at −25° C. (under light protection, normal pressure and with stirring) for 1 to 2 hours until the hydrogen uptake had ended.

Working up

Filtration over Theorit was effected, followed by washing with methanol. The filtrate was neutralized with about 15–20 ml of acetic acid and then evaporated at about 50° C. The residue was taken up in ether and washed with 300 ml of water. The water phase was vigorously shaken 9 times with ether and extracted. The combined ether phases were treated with sodium sulphate and activated charcoal, filtered through Theorit and evaporated at 50° C.

Yield: 27.22 g of oil, that is 74% of the theoretical yield, with reference to (V). The oil was column chromatographed over silica gel with n-hexane with increasing addition of ether (up to 30%) as elution agent.

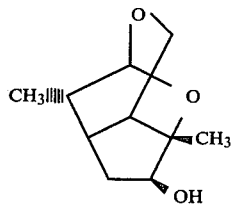

(VII)

Empirical formula: $C_{10}H_{16}O_3$
Molecular weight: 184.23
$[\alpha]_D^{+20°}$: +49° (in Methanol)

EXAMPLE 8

Preparation of 3,10-dimethyl-2,9-dioxatricyclo[4,3,1,0$^{3,7}$]decan-4-one (VIII) from (VII).

10 g of (VII) were dissolved in 268 ml of acetone, 26.8 ml of Jones reagent=oxidation reagent according to the method described in Fieser & Fieser: Reagents for Organic Synthesis, Vol. 1, (1967), 142, were added dropwise at −25° C. with vigorous stirring, then stirring is continued for about a further three minutes.

Working up

After addition of 4.02 ml of isopropanol, stirring was continued for a further 5 minutes and then the mixture was filtered through Theorit and the filter material was thoroughly washed with acetone. The filtrate was neutralized with 3.5 ml of triethylamine and concentrated at 30° C. The residue after evaporation was diluted with double the amount of water and extracted with ether. The ether phase was washed once with saturated potassium carbonate solution. The water phases were then individually extracted 10 times with ether. The combined ether phases were treated with sodium sulphate and activated charcoal, filtered over Theorit and evaporated in a vacuum. Yield: 3.63 g of (VIII) crystallized from ether; that is, 36.6% of the theoretical yield.

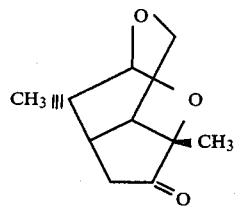

(VIII)

Empirical formula: $C_{10}H_{14}O_3$
Molecular weight: 182.21
m.p.: 139°–140° C. (Kofler, uncorrected)
$[\alpha]_D^{+20°}$: +54° (in Methanol)

EXAMPLE 9

Preparation of 4α-hydroxy-3,10-dimethyl-2,9-dioxatricyclo[4,3,1,0$^{3,7}$]decane (IX) from (VIII).

1.5 g of lithium aluminum hydride were suspended in 90 ml of ether, and a solution of 7.2 g of (VIII) in 36 ml of ether was added dropwise at 0° C., with stirring. Thereafter, the mixture was further stirred for 5 minutes.

Working up

First 180 ml of moist ether were added dropwise to the mixture under nitrogen and with stirring and then, after addition of 6 ml of water, stirring was effected for 10 minutes. Thereafter, the mixture was treated with sodium sulphate and activated charcoal, suction filtered over Theorit and evaporated in a vacuum. The residue was column-chromatographed on silica gel with n-hexane with increasing addition of ether (up to 50%) as elution agent.

Yield: 3.25 g of oily pure product; that is, 44% of the theoretical yield.

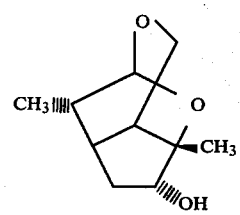

(IX)

Enpirical formula: $C_{10}H_{16}O_3$
Molecular weight: 184.23
$[\alpha]_D^{+20°}$: +29° (in Methanol)

EXAMPLE 10

Preparation of 4β-acetoxy-3,10-dimethyl-2,9-dioxatricyclo[4,3,1,0$^{3,7}$]decane (X) from (VII).

10 g of crude (VII) were dissolved in a mixture of 10 ml of pyridine and 10 ml of acetic anhydride and left to stand over night at room temperature.

Working up 10 ml of ethanol were slowly added to the mixture at 0° C., with stirring, and the mixture was further stirred for 30 minutes at room temperature, evaporated at 80° C. and, after renewed uptake with 20 ml of ethanol, once again concentrated at 80° C. The residue was column-chromatographed on silica gel with n-hexane with increasing addition of ether (up to 20%) as elution agent.

Yield: 4.0 g of oily pure product.

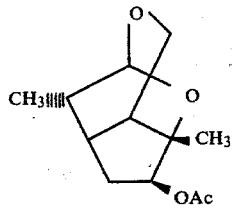
(X)

Empirical formula: $C_{12}H_{18}O_4$
Molecular weight: 226.26
$[\alpha]_D^{+20°}: +56°$ (in Methanol)

EXAMPLE 11

Preparation of 4β-methylcarbamyloxy-3,10-dimethyl-2,9-dioxatricyclo[4,3,1,0$^{3,7}$]decane (XI) from (VII).

5 g of (VII) were dissolved in 50 ml of methylene chloride; 6.8 ml of methyl isocyanate and 1.08 g of phenyl mercury acetate were added and the mixture was then left to stand at room temperature for 1-2 hours.

Working up

After addition of 10 ml of ethanol, evaporation was effected. The residue after evaporation was purified column-chromatographically on silica gel with carbon tetrachloride with increasing addition of chloroform (up to 50%).

Yield: 2.89 g of pure product crystallised from ether; that is, 44.1% of the theoretical yield.

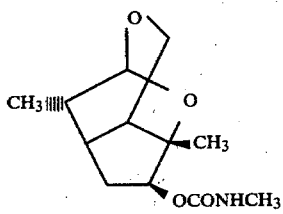
(XI)

Empirical Formula: $C_{12}H_{19}O_4N$
Molecular Weight: 241.27
m.p. 104° C. (Kofler, uncorrected)
$[\alpha]_D^{+20°}: +75°$ (in methanol)

EXAMPLE 12

Preparation of 4α-methylcarbamyloxy-3,10-dimethyl-2,9-dioxatricyclo[4,3,1,0$^{3,7}$]decane (XII) from (IX).

5 g of (IX) were dissolved in 50 ml of methylene chloride; 4.65 ml of methyl isocyanate and 1.08 g of phenyl mercury acetate were added and the mixture was left to stand for about 2 hours at room temperature.

Working up 10 ml of ethanol were added to the mixture and evaporation was effected. The residue after evaporation was then purified column-chromatographically on silica gel and 20-50% strength chloroform in carbon tetrachloride.

Yield: 3.0 g of crystalline (XII); that is, 45.7% of the theoretical yield.

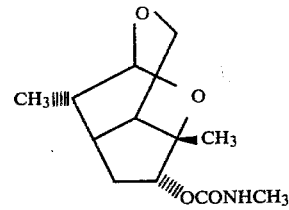
(XII)

Empirical formula: $C_{12}H_{19}O_4N$
Molecular weight: 241.27
m.p.: 109° C. (Kofler, uncorrected)
$[\alpha]_D^{+20°}: +26°$ (in Methanol)

EXAMPLE 13

Preparation of 4-α-acetoxy-3,10-dimethyl-2,9-dioxatricyclo[4,3,1,0$^{3,7}$]decane (XIII) from (IX).

A mixture of 8 ml of pyridine and 8 ml of acetic anhydride was added to 8.0 g of (IX) and the whole was left to stand over night at room temperature.

Working up

The mixture was diluted threefold with chloroform. This solution was first shaken against dilute hydrochloric acid in ice, then with semi-saturated potash solution. The aqueous solutions were then extracted individually with chloroform. The combined chloroform phases were dried with sodium sulphate and treated with activated charcoal. Thereafter, filtration was effected and the filtrate was evaporated in a vacuum. The residue was column-chromatographed on silica gel with n-hexane with increasing addition of ether (up to 30%). (XIII) was able to be crystallised from ether.

Yield: 7.16 g of crystalline product, that is, 73.1% of the theoretical yield.

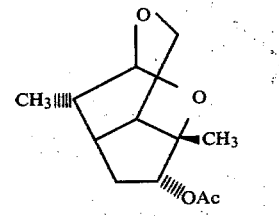
(XIII)

Empirical formula: $C_{12}H_{18}O_4$
Molecular weight: 226.26
m.p.: 85° C.
$[\alpha]_D^{+20°}: +49°$ in Methanol

EXAMPLE 14

Preparation of 4β-isopropylcarbamoyloxy-3,10-dimethyl-2,9-dioxatricyclo[4,3,1,0$^{3,7}$]decane (XIV) from (VII).

1 g of (VII) was dissolved in 9 ml of dichloromethane; 1.8 ml of isopropyl isocyanate and 180 mg of phenyl mercury acetate as catalyst were added and the reaction mixture was subsequently boiled for 2 hours under reflux. After addition of 5 ml of methanol, the mixture was evaporated. The residue after evaporation was column-chromatographed on silica gel with n-hexane with increasing addition of ether (up to 100%).

After concentration of the eluate, 1.1 g of oily isopropyl carbamate were obtained; that is, 75.2% of the theoretical yield.

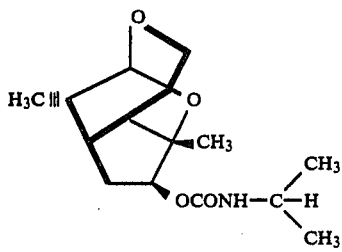

(XIV)

Empirical formula: $C_{14}H_{23}NO_4$
Molecular weight: 269.44
$[\alpha]_D^{22}: +65.5°$ in Methanol

EXAMPLE 15

Preparation of 4β-phenylcarbamoyloxy-3,10-dimethyl-2,9-dioxatricyclo[4,3,1,0$^{3,7}$]decane (XV) from (VII).

1 g of (VII) was dissolved in 9 ml of dichloromethane; 1.8 ml of phenyl isocyanate and 180 mg of phenyl mercury acetate as catalyst were added and the mixture was subsequently stirred for 2 hours at room temperature. After addition of 5 ml of methanol, the mixture was concentrated. The residue after evaporation was column-chromatographed on silica gel with n-hexane with increasing addition of ether (up to 100%). After concentration of the eluate, 1.5 g of crystalline phenyl carbamate were obtained from ether; that is, 91% of the theoretical yield.

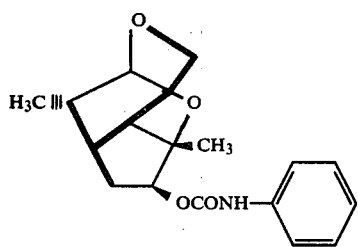

(XV)

Empirical formula: $C_{17}H_{21}NO_4$
Molecular weight: 303.35
m.p.: 240° C.
$[\alpha]_D^{22}: -72.7°$ in Methanol

EXAMPLE 16

Preparation of 4β-n-butylcarbamoyloxy-3,10-dimethyl-2,9-dioxatricyclo[4,3,1,$^{3,7}$]decane (XVI) from (VII).

1 g of (VII) was dissolved in 9 ml of dichloromethane; 1.8 ml of n-butyl isocyanate and 180 mg of phenyl mercury acetate as catalyst were added and the mixture was subsequently stirred for 2 hours at room temperature. After addition of 5 ml of methanol, the mixture was concentrated. The residue after evaporation was column-chromatographed on silica gel with n-hexane with increasing addition of ether (up to 100%). After concentration of the eluate, 0.9 g of oily n-butyl carbamate were obtained; that is, 58.44% of the theoretical yield.

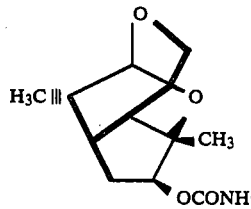

(XVI)

Empirical formula: $C_{15}H_{25}NO_4$
Molecular weight: 283.36
$[\alpha]_D^{22}: +64.0°$ in Methanol

EXAMPLE 17

Preparation of 4β-propionyloxy-3,10-dimethyl-2,9-dioxatricyclo[4,3,1,0$^{3,7}$]decane (XVII) from (VII).

9 g of (VII) were dissolved in a mixture of 9 ml of pyridine and 9 ml of propionic anhydride and left to stand for 4 hours at room temperature.

After dilution with chloroform, ice water was added to the mixture and acidification was effected with dilute hydrochloric acid, followed by shaking.

After separation of the water phase, the chloroform phase was washed once against water and once against dilute soda solution.

The water phases were individually extracted in each case 3 times with chloroform.

After concentration of the chloroform phases, the residue after evaporation was column-chromatographed on silica gel with n-hexane with increasing addition of up to 50% of ether. After evaporation of the eluate, 4.2 g of oily (XVII) were obtained; that is, 36% of the theoretical yield.

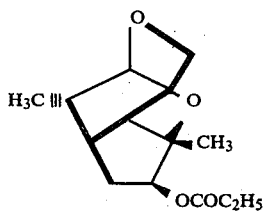

(XVII)

Empirical formula: $C_{13}H_{20}O_4$
Molecular weight: 240.30
$[\alpha]_D^{23}: +67°$ in Chloroform

EXAMPLE 18

Preparation of 4α-isopropylcarbamoyloxy-3,10-dimethyl-2,9-dioxatricyclo[4,3,1,0$^{3,7}$]decane (XVIII) from (IX).

1 g of (IX) was dissolved in 10 ml of dichloromethane; 2 ml of isopropyl isocyanate and 220 mg of phenyl mercury acetate as catalyst were added and the mixture was subsequently left to stand for 10 hours at room temperature. After addition of 5 ml of methanol, the mixture was evaporated. The residue after evaporation was column-chromatographed on silica gel with n-hexane with increasing addition of ether.

After concentration of the eluate, 1.22 g of oily isopropyl carbamate were obtained; that is, 83.5% of the theoretical yield.

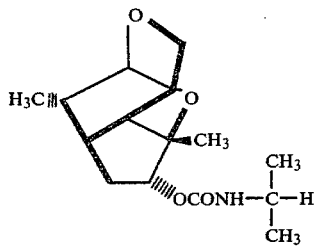

(XVIII)

Empirical formula: $C_{14}H_{23}NO_4$
Molecular weight: 269.44
$[\alpha]_D^{22}: +30°$ in Methanol

EXAMPLE 19

Preparation of 4α-phenylcarbamoyloxy-3,10-dimethyl-2,9-dioxatricyclo[4,3,1,0$^{3,7}$]decane (XIX) from (IX).

1 g of (IX) was dissolved in 10 ml of dichloromethane; 2 ml of phenyl isocyanate and 220 mg of phenyl mercury acetate as catalyst were added and the mixture was subsequently left to stand for 10 hours at room temperature. After addition of 5 ml of methanol, the mixture was concentrated. The residue after evaporation was column-chromatographed on silica gel with carbon tetrachloride with increasing addition of chloroform. After concentration of the eluate, 0.71 g of oily phenyl carbamate was obtained; that is, 43.3% of the theoretical yield.

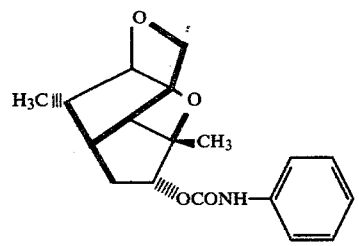

(XIX)

Empirical formula: $C_{17}H_{21}NO_4$
Molecular weight: 303.35
$[\alpha]_D^{22}: +28°$ in Methanol

EXAMPLE 20

Preparation of 4α-n-butylcarbamoyloxy-3,10-dimethyl-2,9-dioxatricyclo[4,3,1,0$^{3,7}$]decane (XX) from (IX).

1 g of (IX) was dissolved in 10 ml of dichloromethane; 2 ml of n-butyl isocyanate and 220 mg of phenyl mercury acetate as catalyst were added and the mixture was subsequently left to stand for 10 hours at room temperature. After addition of 5 ml of methanol, the mixture was evaporated. The residue after evaporation was column-chromatographed on silica gel with n-hexane with increasing addition of ether. After concentration of the eluate, 0.97 g of oily butyl carbamate were obtained; that is, 63% of the theoretical yield.

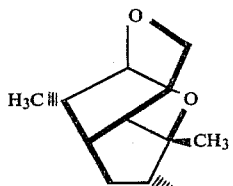

(XX)

Empirical formula: $C_{15}H_{25}NO_4$
Molecular weight: 283.36
$[\alpha]_D^{22}: +45°$ in Methanol

EXAMPLE 21

Preparation of 4α-propionyloxy-3,10-dimethyl-2,9-dioxatricyclo[4,3,1,0$^{3,7}$]decane (XXI) from (IX).

13.36 g of (IX) were dissolved in a mixture of 13.36 ml of pyridine and 13.36 ml of propionic anhydride and left to stand over night at room temperature. After dilution with chloroform, ice water was added to the mixture and acidification was effected with dilute hydrochloric acid; the mixture was then shaken. After separation of the water phase, the chloroform phase was washed once against water and once against dilute soda solution. The water phases were individually extracted in each case 3 times with chloroform.

After concentration of the chloroform phases, the residue after evaporation was column-chromatographed on silica gel with n-hexane with increasing addition of up to 50% of ether. After evaporation of the eluate, 11.35 g of oily (XXI) were obtained; that is, 64.5% of the theoretical yield.

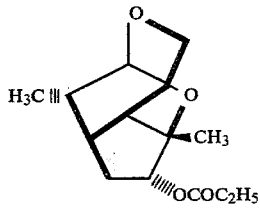

(XXI)

Empirical formula: $C_{13}H_{20}O_4$
Molecular weight: 240.30
$[\alpha]_D^{20}: +30°$ in Chloroform The pharmaceutical properties of the new substances are illustrated in the Table which follows and are compared with the known prior art 8-methoxy-2,9-dioxatricyclo[4,3,1,0$^{3,7}$]decances corresponding individually to the compound of the present invention, as well as other reference substances.

The pharmacological activity of the new compounds differs from that of the known compounds in that the sedative effect is displaced in favor of a stimulating action and an analgesic effect is also present with the new compounds.

The in vivo activity of representative compounds of the present invention was determined as set forth in Table I below by administration to mice in pharmaceutically effective amounts. From the comparative results below, it is demonstrated that, at the same dosage levels in mice, the compounds of the present invention act, in general, more strongly on the nervous system than the prior art compounds. Moreover, the comparative results show an analgesic effect surprisingly superior to that of the prior art compounds.

boxylic anhydride, carboxylic acid chloride, alkyl isocyanate and a carbamic acid ester.

TABLE I

| | PRIOR ART COMPOUNDS 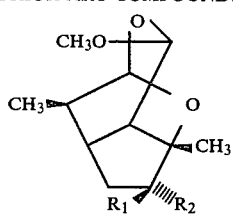 | | | | COMPOUNDS OF THE PRESENT INVENTION 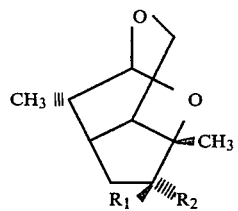 | | | |
|---|---|---|---|---|---|---|---|---|
| Test No. | 1246 | 1561 | 2422 | 2455 | 2619 | 2614 | 2624 | 2648 |
| $R_1$ | OH | H | OH | H | — | OAc | OCONHCH$_3$ | H |
| $R_2$ | H | OH | H | OH | — | H | H | OCONHCH$_3$ |
| $R_1 + R_2$ | — | — | — | — | O | — | — | — |
| LD$_{50}$ i.p.(*) | >800 | >800 | 920 | 406 | 1600 | 822 | 739 | 800 |
| Analgesia ED$_{50}$ p.o.(a)(*) | 68 | 100 | <50 | <10(b) | <10(b) | <50 | <50 | <10 |
| Lowered rectal temp. ED$_{50}$ p.o.(*) | 100 | 100 | 400 | 10 | 25 | 100 | 32 | <100 |

(a) Phenylbenzoquinone test (Writing test)
(b) ≅ Propoxyphene
(*)mg/kg (Mouse)

What is claimed is:

1. A process for the preparation of 2,9-dioxatricyclo[4,3,1,0$^{3,7}$]decane of the general Formula I:

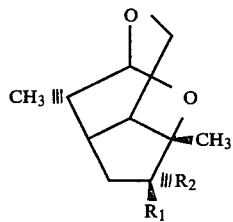

wherein one of $R_1$ and $R_2$ is hydrogen and the other is a hydroxy, acyloxy or carbamyloxy or $R_1$ and $R_2$ together denote oxygen comprising:
   (a) reacting didrovaltratum or an extract containing didrovaltratum with halogen hydride to obtain 8-hydroxy-3-halomethyl-4-acetoxy-10-methylene-2,9-dioxatricyclo[4,3,1,0$^{3,7}$]decane;
   (b) oxidizing the product of (a) to give the lactone of said product;
   (c) converting said lactone with hydrogen on palladium/charcoal to give 1-halomethyl-4-methyl-7-acetoxy-2-oxa-bicyclo[3,2,1]oct-3-en-8-carboxylic acid;
   (d) reducing the product of (c) with a metal hydride to give the primary alcohol of said product;
   (e) converting the product of (d) into 10-halo-10-methyl-3-halomethyl-4-acetoxy-2,9-dioxatricyclo[4,3,1,0$^{3,7}$]decane through oxidative cyclization by means of a halogen in a halogenated hydrocarbon;
   (f) splitting off the halogens with hydrogen on Raney nickel in the presence of a strong base, while simultaneously hydrolyzing the ester to obtain 3,10-dimethyl-4-β-hydroxy-2,9-dioxatricyclo[4,3,1,0$^{3,7}$]decane; and
   (g) converting the product of (f) into the acyloxy or carbamyloxy compound by treating with a compound selected from the group consisting of carboxylic anhydride, carboxylic acid chloride, alkyl isocyanate and a carbamic acid ester.

2. The process of claim 1 wherein didrovaltratum is reacted in step a with halogen hydride in glacial acetic acid.

3. The process of claim 1 wherein step a comprises reacting didrovaltratum or an extract containing didrovaltratum with halogen hydride in alcohol followed by the splitting of the ether bond by means of nitric acid in acetic acid.

4. The process of claim 3 wherein the ether bond of 4-acetoxy-3-iodomethyl-10-methylene-8-alkoxy-2,9-dioxatricyclo[4,3,1,0$^{3,7}$]decane is split to obtain the 8-hydroxy compound.

5. The process of claim 1 wherein step b comprises oxidizing the product of step a with chromic acid to give said lactone.

6. The process of claim 1 wherein the product oxidized in step b is 4-acetoxy-8-hydroxy-3-iodomethyl-10-methylene-2,9-dioxatricyclo[4,3,1,0$^{3,7}$]decane.

7. The process of claim 1 wherein the lactone converted in step c is 4-acetoxy-3-iodomethyl-10-methylene-8-oxo-2,9-dioxatricyclo[4,3,1,0$^{3,7}$]decane.

8. The process of claim 1 wherein the product reduced in step d is 1-iodomethyl-4-methyl-7-acetoxy-2-oxa-bicyclo[3,2,1]oct-3-en-8-carboxylic acid.

9. The process of claim 1 wherein the product converted in step e is 1-iodomethyl-4-methyl-7-acetoxy-8-hydroxymethyl-2-oxa-bicyclo[3,2,1]oct-3-ene (Formula V).

10. The process of claim 1 wherein the product from which halogens are split off in step f is the 4-acetoxy-3-iodomethyl-10-methyl-10-halo-2,9-dioxatricyclo[4,3,1,0$^{3,7}$]decanes of the general Formula VI, in which X is iodine or bromine.

11. The process of claim 1 wherein step f includes oxidation of the 4-hydroxy group of 3,10-dimethyl-4β-hydroxy-2,9-dioxatricyclo[4,3,1,0$^{3,7}$]decane into 3,10-dimethyl-2,9-dioxatricyclo[4,3,1,0$^{3,7}$]decan-4-one followed by reduction of said decanone with a metal hydride to give 3,10-dimethyl-4-α-hydroxy-2,9-dioxatricyclo[4,3,1,0$^{3,7}$]decane.

* * * * *